(12) United States Patent
Nolan

(10) Patent No.: US 8,776,796 B2
(45) Date of Patent: Jul. 15, 2014

(54) APPARATUS AND METHOD FOR IMPROVED ASSISTED VENTILATION

(71) Applicant: CoLabs, Carmel, CA (US)

(72) Inventor: Clay Nolan, Cambria, CA (US)

(73) Assignee: Colabs, Inc., Carmel, CA (US)

( * ) Notice: Subject to any disclaimer, the term of this patent is extended or adjusted under 35 U.S.C. 154(b) by 0 days.

(21) Appl. No.: 13/659,699

(22) Filed: Oct. 24, 2012

(65) Prior Publication Data

US 2013/0146051 A1    Jun. 13, 2013

Related U.S. Application Data

(60) Provisional application No. 61/569,169, filed on Dec. 9, 2011.

(51) Int. Cl.
*A61M 16/04* (2006.01)

(52) U.S. Cl.
USPC .................................. 128/207.14; 126/200.26

(58) Field of Classification Search
USPC ............................ 128/200.26, 207.14–207.17
See application file for complete search history.

(56) References Cited

U.S. PATENT DOCUMENTS

| 4,233,984 | A | * | 11/1980 | Walling | 128/207.14 |
| 4,688,568 | A | * | 8/1987 | Frass et al. | 128/207.15 |
| 5,339,808 | A | * | 8/1994 | Don Michael | 128/207.15 |
| 5,499,625 | A | * | 3/1996 | Frass et al. | 128/207.15 |
| 5,785,051 | A | * | 7/1998 | Lipscher et al. | 128/207.15 |
| 5,832,920 | A | * | 11/1998 | Field | 128/207.14 |
| 5,885,248 | A | * | 3/1999 | Denton | 604/100.03 |
| 6,202,646 | B1 | * | 3/2001 | Camodeca et al. | 128/207.14 |
| 6,584,974 | B1 | * | 7/2003 | Ratner | 128/205.23 |
| 6,923,176 | B2 | * | 8/2005 | Ranzinger | 128/200.26 |
| 6,994,087 | B1 | * | 2/2006 | Smith | 128/207.16 |
| 7,178,519 | B2 | * | 2/2007 | Melker et al. | 128/200.26 |
| 7,503,328 | B2 | * | 3/2009 | Kolobow et al. | 128/207.14 |
| 7,747,319 | B2 | * | 6/2010 | Freeman | 607/6 |
| 2004/0020491 | A1 | * | 2/2004 | Fortuna | 128/207.15 |
| 2007/0221222 | A1 | * | 9/2007 | Lurie | 128/204.18 |
| 2008/0029100 | A1 | * | 2/2008 | Glassenberg et al. | 128/207.15 |
| 2008/0072913 | A1 | * | 3/2008 | Baker et al. | 128/207.15 |
| 2008/0176199 | A1 | | 7/2008 | Stickney et al. | |
| 2009/0277447 | A1 | | 11/2009 | Voss et al. | |
| 2010/0163023 | A1 | * | 7/2010 | Singh | 128/200.26 |
| 2010/0242957 | A1 | | 9/2010 | Fortuna | |
| 2012/0024292 | A1 | * | 2/2012 | Sandmore et al. | 128/207.14 |

FOREIGN PATENT DOCUMENTS

WO    WO 2011/126812    10/2011
WO    WO 2013/086134    6/2013

* cited by examiner

*Primary Examiner* — Justine Yu
*Assistant Examiner* — LaToya M Louis
(74) *Attorney, Agent, or Firm* — Levine Bagade Han LLP

(57) ABSTRACT

Devices and methods for allowing for improved assisted ventilation of a patient. The methods and devices provide a number of benefits over conventional approaches for assisted ventilation. For example, the methods and devices described herein permit blind insertion of a device that can allow ventilation regardless of whether the device is positioned within a trachea or an esophagus.

26 Claims, 18 Drawing Sheets

|  | Component | Description | Part | | |
|---|---|---|---|---|---|
| 1 | M1 | Operation Valve | Clippard TV-4DP or Equiv | | |
| 2 | M2 | Mode Valve | TV-4DMP | | |
| 3 | P1 | Medial Supply Valve | MJV-4, Pilot MVA-10 | | |
| 4 | P2 | Distal Supply Valve | MJV-4, Pilot MPA-3 | | |
| 5 | P3 | Pulse Valve | FV-3P, Pilot MPA-10 | | |
| 6 | P4 | Ventilation Selector Valve | FV-3P, Pilot MPA-3 | | |
| 7 | F1 | Reset Timing Flow Control Valve | JFC-3AR | | |
| 8 | F2 | Pulse Timing Flow Control Valve | JFC-3AR | | |
| 9 | F3 | On-Demand Flow Control Valve | (10-32 threads) | | |
| 10 | E1 | Accumulator Quick Exhaust | MEV-2 | | |
| 11 | S1 | Ventilation Supply Shuttle Valve | MSV-1444 | | |
| 12 | S2 | Vacuum Supply Shuttle Valve | MSV-1444 | | |
| 13 | R1 | Pulse Pressure Relief Valve | Smart Products, 2x15psi | | |
| 14 | R2 | Pulse Pilot Relief Valve | Smart Products, 0.5psi | | |
| 15 | I1 | Medial Ventilation Indicator | IND-3G | | |
| 16 | I2 | Distal Ventilation Indicator | IND-3G | | |
| 17 | I3 | Vacuum Indicator | IND-3G | | |
| 18 | G1 | Vacuum Generator | SMC | | |
| 19 | V1 | Pulse Accumulator | MAT-4.0 | | |

*FIG. 8B*

| | Manual Valve | | Pilot Valve | | | | Indicator | | | Output | | | |
|---|---|---|---|---|---|---|---|---|---|---|---|---|---|
| Operational Mode | 1 | 2 | 1 | 2 | 3 | 4 | 1 | 2 | 3 | V | M | D | |
| 0 | 2 | (any) | N/A | N/A | N/A | N/A | OFF | OFF | OFF | | | | |
| 1 | 3 | (any) | N/A | N/A | N/A | N/A | OFF | OFF | ON | v | | | |
| 2 | 1 | 1 | 1 | 1 | N/A | N/A | OFF | OFF | ON | v | | | |
| 3A | 1 | 1 | 1 | 2 | 1 | 2 | OFF | ON | OFF | | | | |
| 3B | 1 | 1 | 1 | 2 | 2 | 2 | OFF | ON | OFF | | | v | Fixed Vol |
| 4A | 1 | 1 | 2 | 1 | 1 | 1 | ON | OFF | ON | v | | | |
| 4B | 1 | 1 | 2 | 1 | 2 | 1 | ON | OFF | ON | v | v | | Fixed Vol |
| 5 | 1 | 2 | 1 | 2 | N/A | 2 | OFF | ON | OFF | | | | |
| 6 | 1 | 3 | 1 | 2 | N/A | 2 | OFF | ON | OFF | | | v | Continuous |
| 7 | 1 | 2 | 2 | 1 | N/A | 1 | ON | OFF | ON | v | | | |
| 8 | 1 | 3 | 2 | 1 | N/A | 1 | ON | OFF | ON | v | v | | Continuous |

*FIG. 8C*

APPARATUS AND METHOD FOR IMPROVED ASSISTED VENTILATION

CROSS-REFERENCE TO RELATED APPLICATIONS

The present application is a non-provisional application of U.S. provisional application No. 61/569,169 filed Dec. 9, 2011, the content of which is incorporated herein by reference in its entirety.

BACKGROUND OF THE INVENTION

Intubation is the placement of a tube of an intubation device into an airway lumen of the body of a patient to provide assisted ventilation of the lungs to maintain a supply of oxygen to the blood in those cases where the patient is unable to breathe on his or her own. Intubation in cases of respiratory distress involves the placement of a tube into the trachea of the patient. Tracheal intubation also involves the positioning of an endotracheal tube into a patient's trachea through the vocal cords, so the caregiver must also be careful to avoid injuring the vocal cords. In many cases, care must be taken when intubating a patient since improper placement of the tube can result in additional harm to the patient. For example, many conventional intubation devices rely on an inflatable cuff that forms a seal against the lumen wall to maintain a position of the tube within the lumen. Over-inflation of the cuff, can cause internal bleeding in the patient. Another significant problem is that extreme care must be taken to avoid positioning the intubation tube within the esophagus rather than the trachea. In such cases, with conventional devices, the first responder or medical practitioner cannot properly ventilate the patient and the patient can suffer further injury.

Even properly trained medical caregivers and first responders must proceed with caution during intubation to avoid misplacement of the intubation device or to avoid unwanted insertion errors and risk of injury. Delay and/or misplacement of the endotracheal tube, such as misplacement of the endotracheal tube into the esophagus, can potentially result in neurological damage or death. Improper positioning of the endotracheal tube also can compromise airway protection or result in inadequate ventilation. It is therefore imperative to intubate a patient quickly and position the endotracheal tube correctly when a medical condition arises.

To reduce the risk of complications during intubation, the caregiver, whether a first responder, such as an emergency medical technician, paramedic, or a nurse or physician must proceed as quickly as possible yet with caution to avoid the potential complications. In addition, a first responder must often attempt to intubate the patient in a less than desirable location such as a bathroom, restaurant, or other area not conducive to providing proper medical treatment and care.

Assisted ventilation in cases of cardiac arrest also requires prompt and accurate placement of an intubation device within the trachea so that chest compressions can occur. In such cases, intubation allows for ventilation of the lungs and a supply of oxygen to the blood while chest compressions provide circulation of the blood.

The American Heart Association's protocols for cardio pulmonary resuscitation (CPR) previously required pausing after every fifteen chest compressions to allow for two ventilations. The American Heart Association's 2010 protocols decreased the frequency of ventilations such that chest compressions are to be paused after every thirty compressions to allow for two ventilations. It is believed that the main reasons supporting the change in protocol are: 1) reduce the amount of intra-thoracic pressure associated with positive pressure ventilations since positive pressure ventilations decrease the efficiency of the heart; and 2) to minimize the interruptions of chest compressions to maintain constant arterial pressure. Accordingly, now most caregivers only simultaneously ventilate the patient and provide compressions if the patient is properly intubated.

FIG. 1 provides a partial view of a patient's oral cavity 10, tongue 12 and pharynx 14 where the pharynx 14 is the membrane-lined cavity at the rear of the oral cavity 10. The pharynx 14 includes openings of the esophagus 16 and trachea 18. As shown, the openings to the esophagus 16 and trachea 18 are adjacent to one another. When a medical caregiver attempts to intubate a patient, the caregiver shall attempt to position the intubation device within the trachea 18 to provide oxygen to the lungs 2. As noted above, the caregiver shall attempt to avoid positioning the intubation device within the esophagus 16 and in doing so often must proceed slowly and with caution to avoid causing undesired trauma to vocal cords or other structures within the body.

The wall of the esophagus 16 is composed of striated and smooth muscle. Since the esophagus 16 relies on peristalsis to move food downward towards the stomach, the walls of the esophagus 16 are naturally compliant and do not have any structural reinforcement. The trachea 18, on the other hand, is relatively stronger and is naturally designed not to collapse given its function of transporting air to the bronchi and lungs 2. The wall of the trachea 18 includes a number of cartilaginous semicircular rings 20 that prevent the trachea 18 from collapsing. The trachea 20 lies anteriorly to the esophagus 16 where the openings of the esophagus 16 and trachea are separated by a tiny flap, the epiglottis 22. The epiglottis 22 protects the trachea when the individual swallows food or other substances.

FIG. 2 illustrates a conventional device 50 used for intubating a patient. As shown, the device 50 is inserted through the mouth and oral cavity into the trachea 18. The caregiver must navigate the device 50 into the trachea 18 rather than the esophagus while traversing the epiglottis 22 and vocal cords 24. The caregiver must take particular care to avoid causing damage to the vocal cords 24. Once properly positioned, the caregiver can optionally inflate 52 a balloon on the device 50 to anchor the device within the trachea 18. After the caregiver confirms placement of the device 50, ventilation of the patient can take place.

Presently, the Combitube, supplied by Nellcor, is commonly used for airway management. The Combitube, also known as a double-lumen airway, is a blind insertion airway device (BIAD) used by first responders as well as in an emergency room setting. The Combitube is intended to allow for tracheal intubation of a patient in respiratory distress by use of a cuffed, double-lumen tube. The double lumen tube is inserted into the patient's airway to allow for ventilation of the patient's lungs. Inflation of the cuff allows the device to function similarly to an endotracheal tube and usually closes off the esophagus, allowing ventilation and preventing pulmonary aspiration of gastric contents.

However, placement of traditional intubation devices is very difficult due to the risk of improperly positioning the device. The risk of a device being improperly positioned can be fatal if not recognized. The conventional devices described above require positioning by an individual that is well trained in positioning such devices. Furthermore, even well trained individuals must proceed with caution when placing conventional devices.

There remains a need for a ventilation device and/or system that can effectively ventilate individuals and can be effectively positioned with minimal training required by the caregiver.

SUMMARY OF THE INVENTION

The present disclosure includes devices and method allowing for improved assisted ventilation of a patient. The methods and devices provide a number of benefits over conventional approaches for assisted ventilation. For example, the methods and devices described herein permit blind insertion of a device that can allow ventilation regardless of whether the device is positioned within a trachea or an esophagus. Some variations of the devices and methods allow minimally trained bystanders and laypersons to place an advanced airway for assisted ventilation. The devices described herein can be designed such that a single size can accommodate a variety of patient sizes thereby reducing the number of devices of varying sizes that must be kept in inventory. Additionally, having devices 1 that can accommodate a wide range of individuals reduces the need of a first responder to assess the anatomic features of a patient prior to acting on the patient. Patients undergoing cardiac distress, high frequency ventilation can result in elevated intrathoracic pressure. Elevated intrathoracic pressure can ultimately reduce the effectiveness of chest compressions. Variations of the current device and methods allow for controlled ventilation, which avoids high frequency ventilation.

In certain variations the methods and devices described herein further allow for a caregiver to perform continuous compressions simultaneous with insertion of the device into the patient. Furthermore, the devices and methods allow for ventilation without the need to stop compressions. Variations of the methods and devices allow for reducing the number of people required to perform CPR.

Variations of the devices described herein permit a patient to breathe on his/her own if spontaneous respiration resumes. Moreover, if a device is inserted into a patient that is not in respiratory arrest, the patient can continue to breath due to the amount of time that the device is in an inspiration phase.

In one example a method for ventilating an individual can include inserting a ventilation device within a natural respiratory opening of the individual by advancing a working end of the ventilation device within a body passageway of the individual, where the working end includes a distal opening fluidly coupled to a first lumen and a medial opening fluidly coupled to a second lumen; drawing suction drawing suction through the distal opening and maintaining the suction for a period of time; determining a ventilation lumen from the first lumen or second lumen by selecting the first lumen as the ventilation lumen if the tissue of the body passageway does not seal the first opening; or selecting the second lumen as the ventilation lumen if the tissue of the body passageway seals the first opening; and ventilating the patient through the ventilation lumen.

Another variation of a method under the present disclosure includes a method for rapidly ventilating an individual experiencing respiratory distress by inserting a ventilation device within a natural respiratory opening of the individual by advancing a working end of the ventilation device within a body passageway of the individual, where the working end includes a distal opening fluidly coupled to a first lumen and a medial opening fluidly coupled to a second lumen; pulling a suction force through the distal opening and maintaining the suction force for a period of time; and ventilating the individual through the first lumen in the event that tissue from the body passageway does not seal the distal opening, and alternatively, ventilating the individual through the second lumen in the event that tissue from the body passageway seals the distal opening.

The present disclosure also includes devices ventilating an individual through one or more body passageways. For example, such a device can comprise: a tubular member having at least a first and second lumen, where the first lumen is fluidly coupled to a first opening located towards a distal portion of the tubular member, the second lumen fluidly coupled to a medial opening being located proximally to the first opening along a wall of the tubular member, where the first opening and medial opening are fluidly isolated within the tubular member; a control system having a suction source and a gas supply lumen, the control system having a valve configured to fluidly couple the ventilation source to either the first lumen or to the second lumen; the control system also capable of drawing suction through the first opening and first lumen, where the control system is configured to identify formation of a seal at the first opening; where the control system is further configured selectively form a ventilation path from the supply lumen to the first lumen or second lumen by selecting the first lumen as the ventilation path if the seal at the first opening fails to form; or selecting the second lumen as the ventilation path if the seal forms at the first opening; and where the control system is capable of ventilating the individual through the ventilation path.

The ventilation systems described herein can be configured to work with other rescue devices. For example, the ventilation system can be configured to work with an active chest compression device so that ventilations and chest compressions are timed to increase effectiveness of both the compression and ventilation. The coupling can be mechanical and/or electrical. The ventilation system can also include carbon dioxide sampling so that carbon dioxide levels are outputted via a signal or gas stream to a monitor or other notification means as described herein.

Variations of the methods and devices described herein can include adjusting ventilation parameter to improve ventilation of the individual. Such parameters can include a ventilation rate, volume, pressure, inhale and exhale ratios, and PEEP.

The methods and devices can include further providing an indicator signal to identify desired times of chest compression. Such signals can include an audible signal, a visual signal, and/or a tactile signal.

Variations of the device can include an anchor, such as an inflatable balloon, that temporarily secures the ventilation device in a body passageway. In some variations the balloon can be coupled to the working end of the ventilation device.

Variations of the device can include a face mask or other structure that is used to aid insertion of the device by allowing the caregiver to easily identify an orientation of the device. Alternatively, the face mask or other structure can allow the caregiver to affix the device to the individual.

Variations of the devices described herein can include a proximal portion that comprises a reinforced section to prevent collapse of the ventilation device in a mouth of the individual. Devices can optionally include a pressure relief valve to adjust ventilation parameters of the individual. Additional variations of devices can comprise a plurality of markings on an exterior surface and where inserting the ventilation device into the natural respiratory opening comprises advancing the ventilation device to a depth determined by one or more markings. The ventilation system can also adjust ventilation parameters based on carbon dioxide of the patient or pulse oximetry. Alternatively or in addition, carboximetry and/or oximetry systems can be coupled to the system.

The system and methods described herein can be compatible with devices that monitor the concentration or partial pressure of carbon dioxide (CO2) in the respiratory gases (capnography). Primarily such devices are monitoring tool for use during anesthesia and intensive care that monitor expiratory CO2 are of interest when rebreathing systems are being used. The ability to integrate the ventilation systems described herein with such capnography systems allows for improved patient care. Furthermore, the systems and methods described herein can be compatible with equipment found in emergency vehicles such as oxygen supplies and/or power supplies. In some variations, the system of the present disclosure can also provide audio or even video (through use of a display screen) instructions to ensure proper operation in those situations where the system may be used by first responders that are not trained emergency personnel.

BRIEF DESCRIPTION OF THE DRAWINGS

The invention is best understood from the following detailed description when read in conjunction with the accompanying drawings. It is emphasized that, according to common practice, the various features of the drawings are not to-scale. On the contrary, the dimensions of the various features are arbitrarily expanded or reduced for clarity. Also for purposes of clarity, certain features of the invention may not be depicted in some of the drawings. Included in the drawings are the following figures:

FIG. 8B provides a component listing for the schematic of FIG. 8A.

FIG. 8C shows a listing of various modes for the system.

DETAILED DESCRIPTION OF THE INVENTION

Before the devices, systems and methods of the present invention are described, it is to be understood that this invention is not limited to particular therapeutic applications and implant sites described, as such may vary. It is also to be understood that the terminology used herein is for the purpose of describing particular embodiments only, and is not intended to be limiting, since the scope of the present invention will be limited only by the appended claims.

Unless defined otherwise, all technical and scientific terms used herein have the same meaning as commonly understood by one of ordinary skill in the art to which this invention belongs. The terms "proximal", "distal", "near" and "far" when used indicate positions or locations relative to the user where proximal refers to a position or location closer to the user and distal refers to a position or location farther away from the user.

Figure 1:
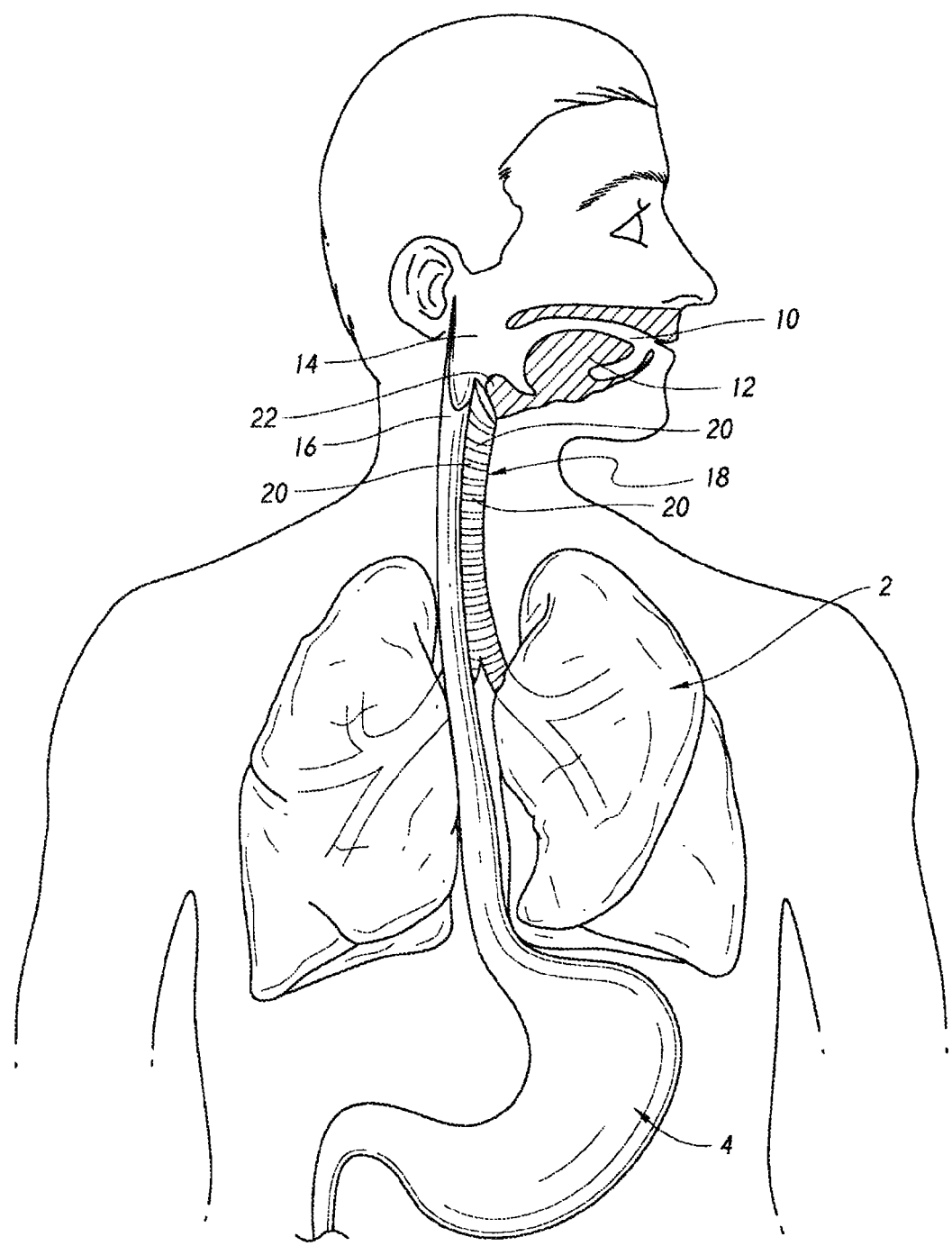
FIG. 1 provides a partial view of a patient's oral cavity, tongue, pharynx as well as esophagus and trachea.
Figure 2:
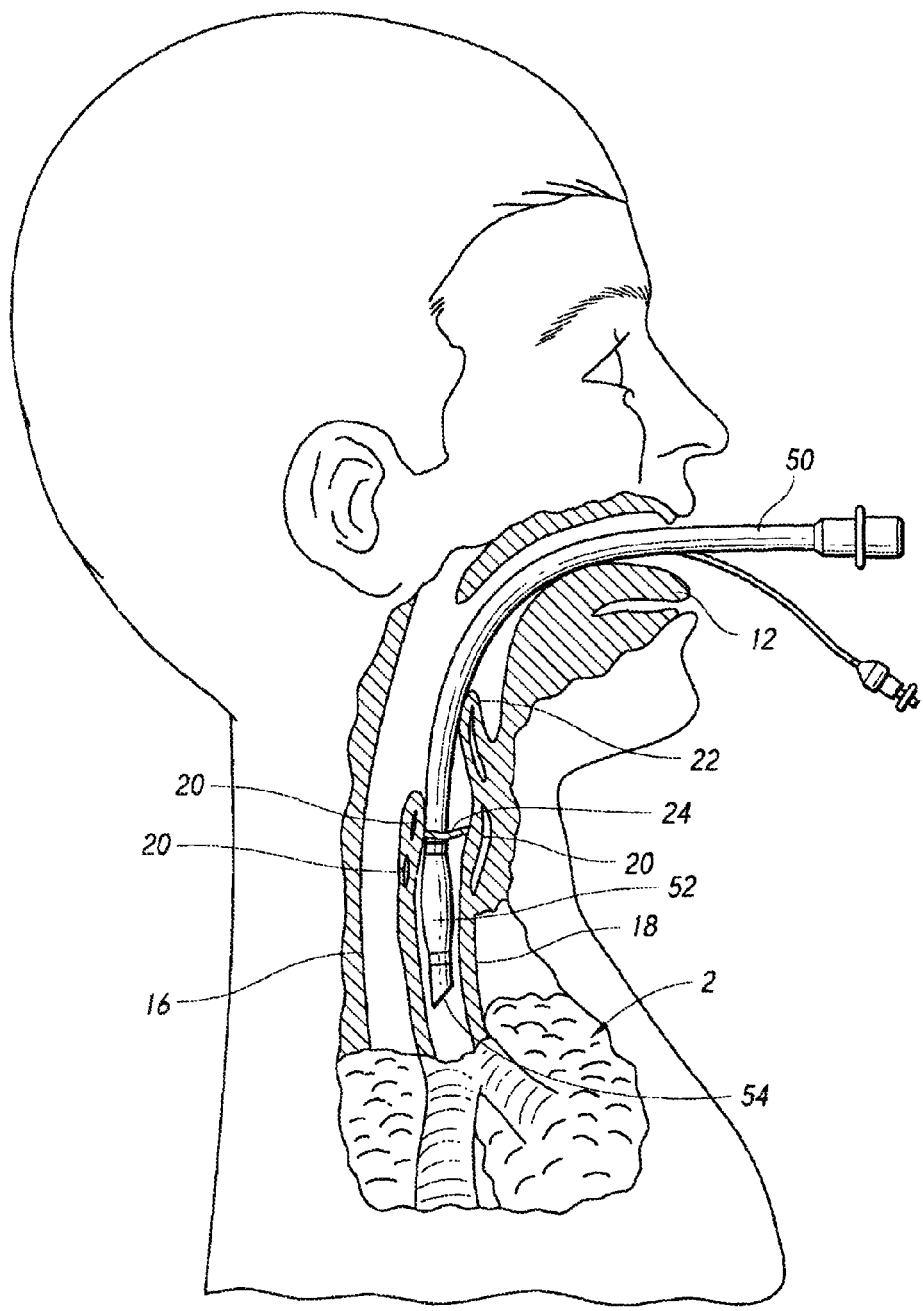
FIG. 2 illustrates one example of a conventional device as used to intubate a patient.
Figure 3:
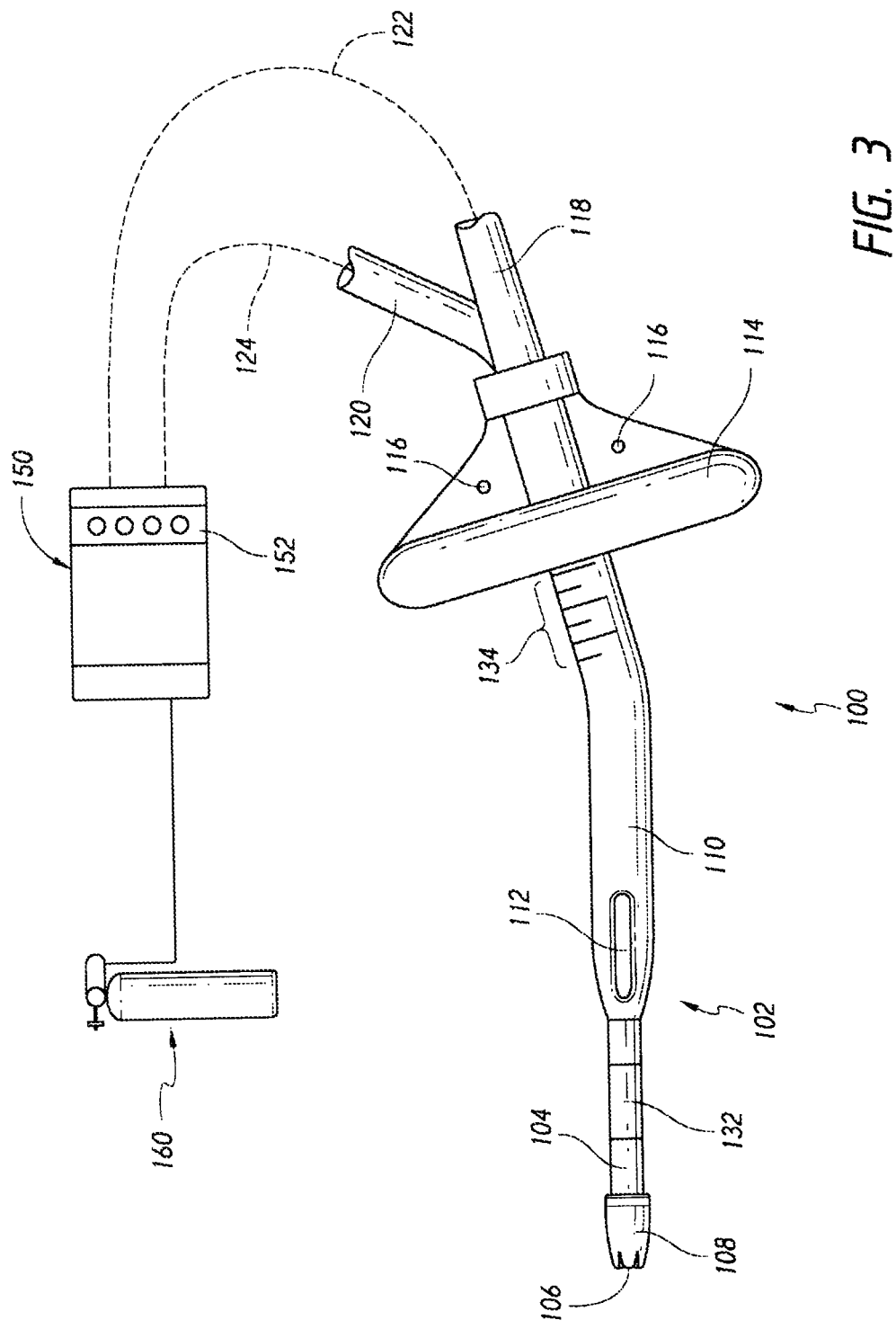
FIG. 3 illustrates various components of an example of an improved ventilation system.

FIG. 3 illustrates various components of an example of an improved system according to the present disclosure. As shown, the ventilation device 100 includes a working end 102 that is inserted into a patient. The working end can include a distal tubing 104 that contains a first lumen (not shown), which extends through a distal opening 106 of the ventilation device 100 and is in fluid communication with a control unit (also called a ventilator) 150 and/or supply source 160 via one or more proximal tubes 118. The control unit 150 can also include an apparatus designed to provide suction as well as a collection canister. In operation, the control unit 150 directs suction or applies a vacuum through a first fluid path 122, which in turn causes a suction or negative pressure at the distal opening 106. The source 160 can comprise oxygen, air, or any other gas that is desired for ventilation of delivery into the lungs. The source 160 can be nested within physical construct of the controller 150. However, the source 160 can be optional so that the controller ventilates the patient only using ambient air.

The control unit 150 maintains the device 100 in this state for a set period of time and monitors the parameters of the pressure or flow parameters within the first lumen to determine whether to ventilate through the first or second. The example illustrated in FIG. 3 also includes a hub 108 with one or more features that aid in proper functioning of the device. Such features are described in detail below. Furthermore, the distal opening 106 can include any number of ports at the distal end of the device so long as the ports are in a fluid path with the first lumen. Likewise, the medial opening 112 can comprise any number of openings as long as those openings are in fluid communication with the second lumen. In addition, variations of the device can also be inserted through a nasal opening rather than a mouth.

The ventilation device 100 further includes a proximal tubing 110 that houses a second lumen (not shown) that exits the device 100 at a medial opening 112. As discussed below, distal opening and first lumen are fluidly isolated from the medial opening and second lumen through the working end of the device 102 to the control unit 150. This fluid isolation allows the control unit 150 to determine which lumen to use to ventilate the patient. The control unit directs flow through a second fluid path 124 that is fluidly coupled to the second lumen and medial opening 112 when the device is positioned in the esophagus 16 rather than the trachea 18.

The ventilation system 100 illustrated in FIG. 3 also shows an optional mask 114 with optional venting ports 116. Variations of the system can include alternate configurations without a mask or with other such devices such as a mouth guard or any other commonly used mounting apparatus. As discussed below, the mask 114 or other mounting apparatus can be used to assist the caregiver in properly orienting the device 100 as it is inserted into the patient. Variations of the device can include a balloon, sponge or any other structure that secures the proximal region of the device to the patient to ensure that gas is directed to the lungs during inhalation. The mask (or other structure as described herein) can include a securing band, tape strip, or temporary adhesive to secure the mask in place on the patient. The mask or similar feature can be used to determine how far to advance the working end 102 into the patient. Alternatively or in combination, the device 100 can include graduated markings 134 to assist the caregiver in properly advancing the device into the patient.

FIG. 3 also shows a representative figure of a control system 150 with a number of controls 152 that allow for various device operative sequences, manual controls, or device overrides. For example the system 150 can include manual ventilation controls so that the caregiver can manually adjust inspiration and expiration of the patient. The controls 152 can include a reset or rapid ventilation mode for performing cardio pulmonary resuscitation. The controls 150 include a continuous airflow or continuous vacuum mode that can assist in clearing debris or bodily fluids from the body passages. The controls also allow caregivers to connect the device 100 directly to an endotracheal tube if the caregiver decides to intubate. In an additional variation, the system can allow for active ventilation consisting of blowing for a period and then sucking for a period through the active lumen in order to increase ventilation efficiency.

In additional variations, the control system 150 can be integrated into one or more parts of the device body 102 rather than being a separate stand-alone box type configuration. In addition, the ventilation system 100 can be optionally configured to work with a defibrillator. Alternate variations of the system 100 can be configured to provide an audible, visual, or tactile sensation to indicate when a caregiver should administer chest compressions.

FIG. 3 also shows the depicted variation of the device 100 as having an optional balloon 132 or other expandable member located on a working end. When used, the balloon can be positioned anywhere along the device adjacent to the distal opening 106. Alternatively, or in combination, a balloon can be located adjacent to the medial opening.

The various tubing forming the device 100 should be sufficiently flexible so that the device can be navigated through the upper respiratory system. Alternatively, or in addition, portions of the tubing can be constructed to withstand being collapsed by the patient's mouth or teeth. In additional variations the system 100 can be designed such that the distance between the distal opening 106 is adjustable relative to the medial opening 112 and/or the mask 114 (or even moveable relative to the gradiations 134). A similar variation includes a medial opening 112 that can be adjustably positioned relative to the distal opening 106, mask 114 and or gradiations 134

Figure 4A:
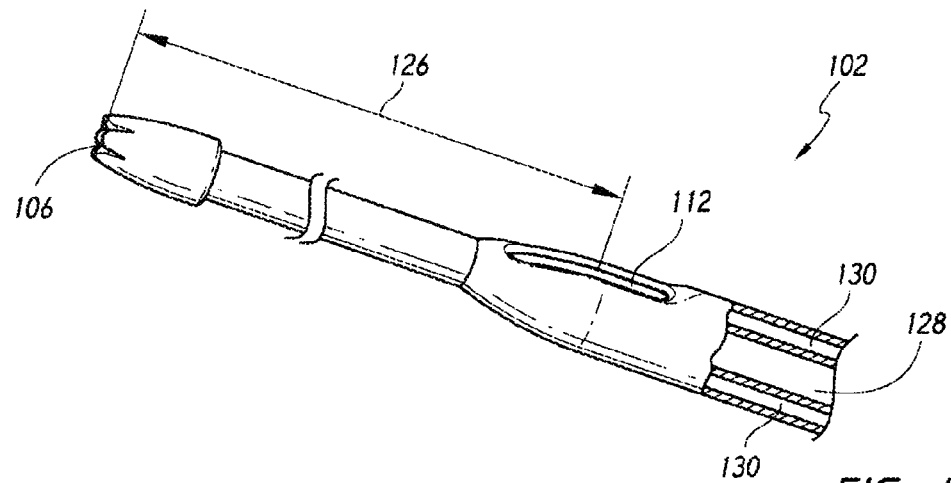
FIGS. 4A to 4C illustrate a partial sectional view of a working end of an improved ventilation device.
Figure 4B:
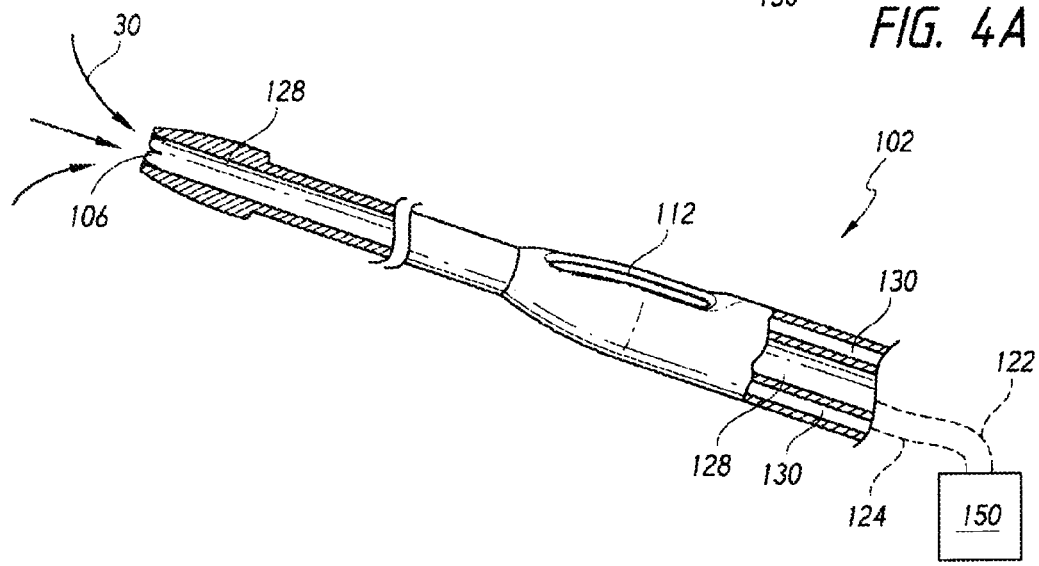
Figure 4C:
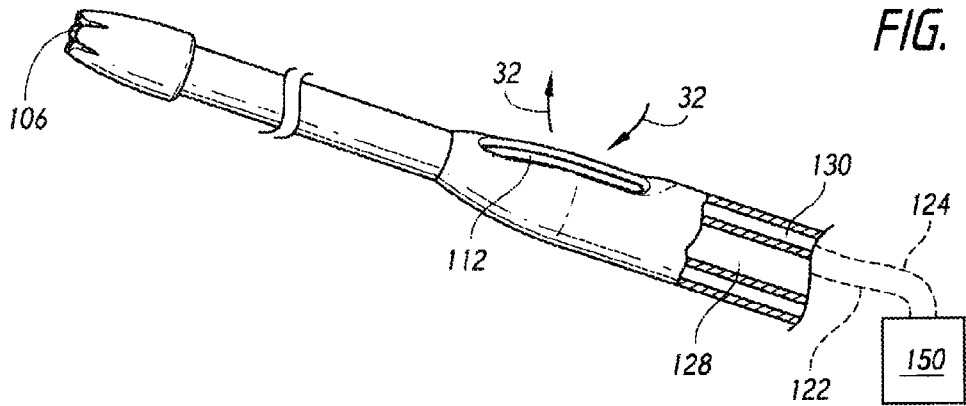

FIGS. 4A to 4C illustrate a partial sectional view of an airway unit or working end 102 of a ventilation device 100 as described herein.

FIG. 4A illustrates a first lumen 128 that is fluidly coupled to a distal opening 106 and a second lumen 130 that is fluidly coupled to the medial opening 112 where the first and second lumens 128 and 130 are fluidly isolated from each other as described above. FIG. 4A also illustrates that the spacing 126 between the distal opening 106 and the medial opening 112 can be selected based on the intended patient. For example, since the medial opening 112 is intended to be positioned in or around the pharynx when the distal opening 106 is positioned in the esophagus or trachea, the spacing 126 can be selected for an individual of average build. In most cases, the working end 102 of the ventilation device 100 will comprise a single use disposable component. Accordingly, the ventilation device 100 can include a number of disposable components having different spacing 126 between the medial 112 and distal 106 openings. For instance, the varying spacing can accommodate infants, toddlers, young children, as well as various body sizes.

FIG. 4B illustrates a partial cross sectional view of the working end 102 of the ventilation device of FIG. 4A. Once the device is properly positioned within the patient, the control unit 150 applies a suction or vacuum through a first fluid path 122, then through the first lumen 128 and ultimately causing a vacuum at the distal opening 106 as denoted by arrows 30. In additional variations, the operator or caregiver may choose to clear food or other debris from the patient by delivering air through the first lumen 128 or by attempting to use the suction at the distal opening to remove particles or other bodily fluids. The system 150 shall continue to pull a vacuum through the first lumen 130 for a period of time. If the device 100 is properly positioned within the trachea (as discussed below), the system 150 will begin to ventilate through the first lumen 128. In other words, the system 100 will begin to cyclically deliver oxygen or other gas from the source 160 and remove carbon dioxide from the patient to properly ventilate the patient's lungs. In this situation, flow is not required through the second lumen 130 and medial opening 112. Although FIG. 4B shows the first lumen 128 to be located within the second lumen 130 any number of variations can be used. For example, the lumens can be concentric or parallel. Additional variations even allow for the lumens to be in fluid communication where one or more valves determine whether ventilation occurs through the distal opening or through the medial opening.

The system 150 can comprise the mechanism that ventilates and produces suction or a vacuum. Generally, the system 150 is reusable (as opposed to the working end that is generally disposable). The system 150 can be portable, affixed to an ambulance or other emergency vehicle or build within a cart or room. Variations include battery powered devices, pneumatic powered devices, or devices that require a power source (such as an AC outlet).

FIG. 4C illustrates the condition where the distal opening 106 is positioned within the esophagus. In this situation the control unit 150 directs ventilation through the second lumen 130. As shown by arrows 32, because the medial lumen 112 is fluidly coupled to the second lumen 130 ventilation 32 takes place at the medial opening 112.

FIGS. 5A to 5E show a representation of the process of ventilating a patient using a ventilation device 100 as described herein.

Figure 5A:
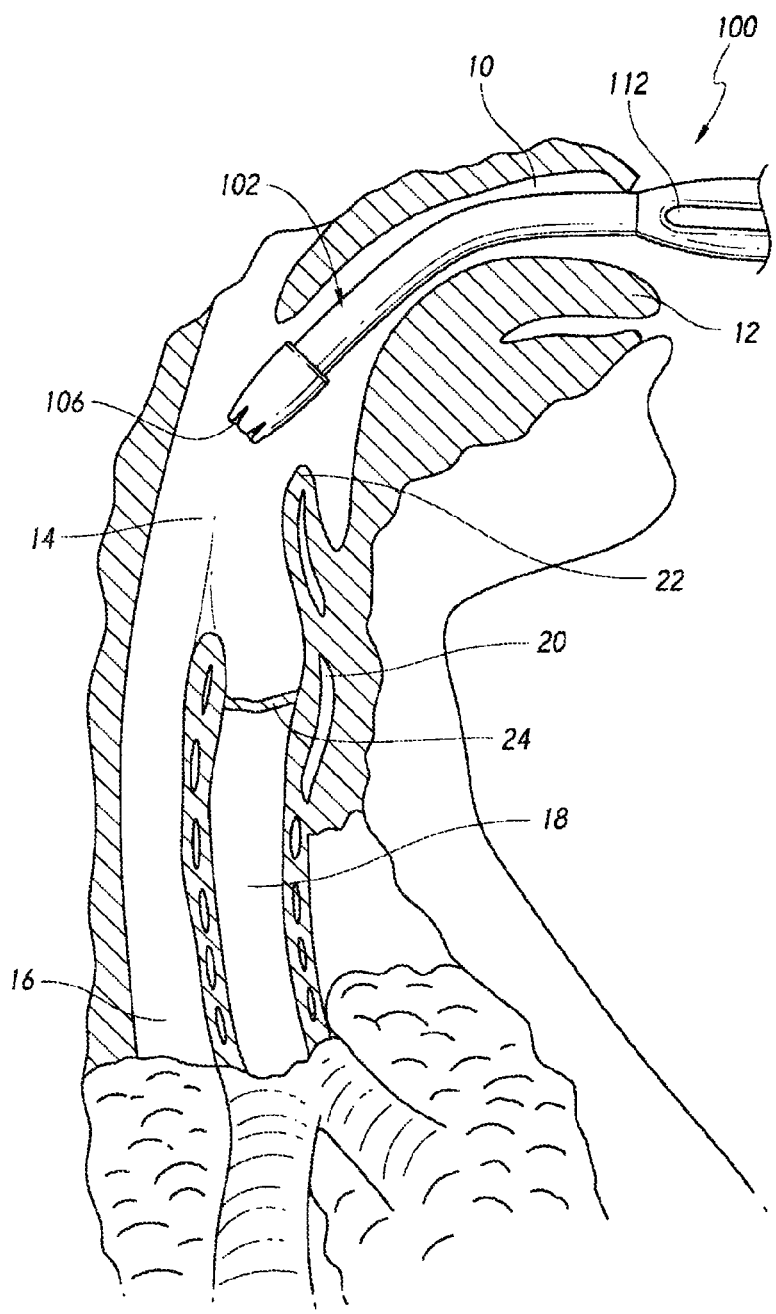
FIGS. 5A to 5E show a representation of the process of ventilating a patient using an improved ventilation device.

FIG. 5A illustrates the ventilation device 100 as a caregiver advances the device 100 into the oral cavity 10 over the tongue 12 and into the pharynx 14. At any time during the procedure, the caregiver can manually operate the device to suction fluids, food particles, or other items from the body. As described herein, the caregiver can "blindly" advance the working end 102 into the patient. As a result, the working end 102 will either end up in the esophagus 16 or trachea 18 of the patient.

Figure 5B:
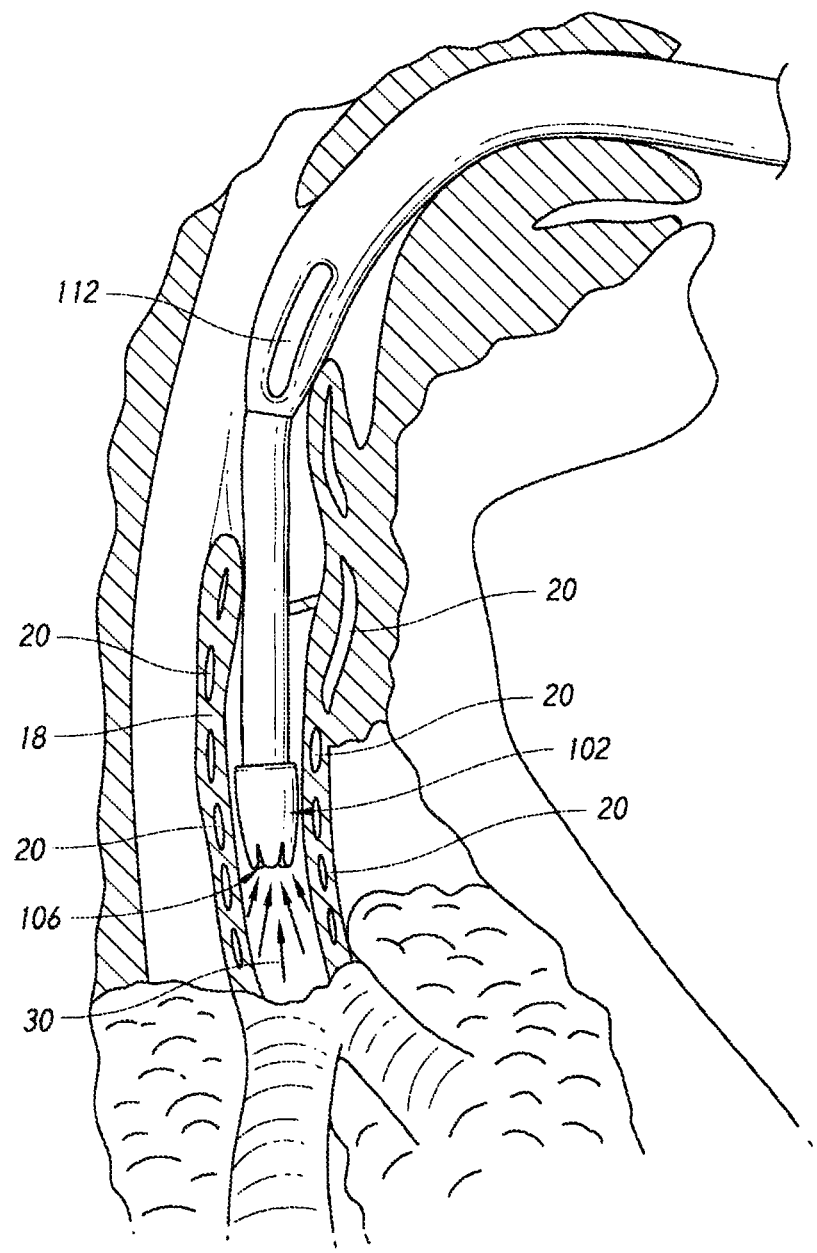
Figure 5C:
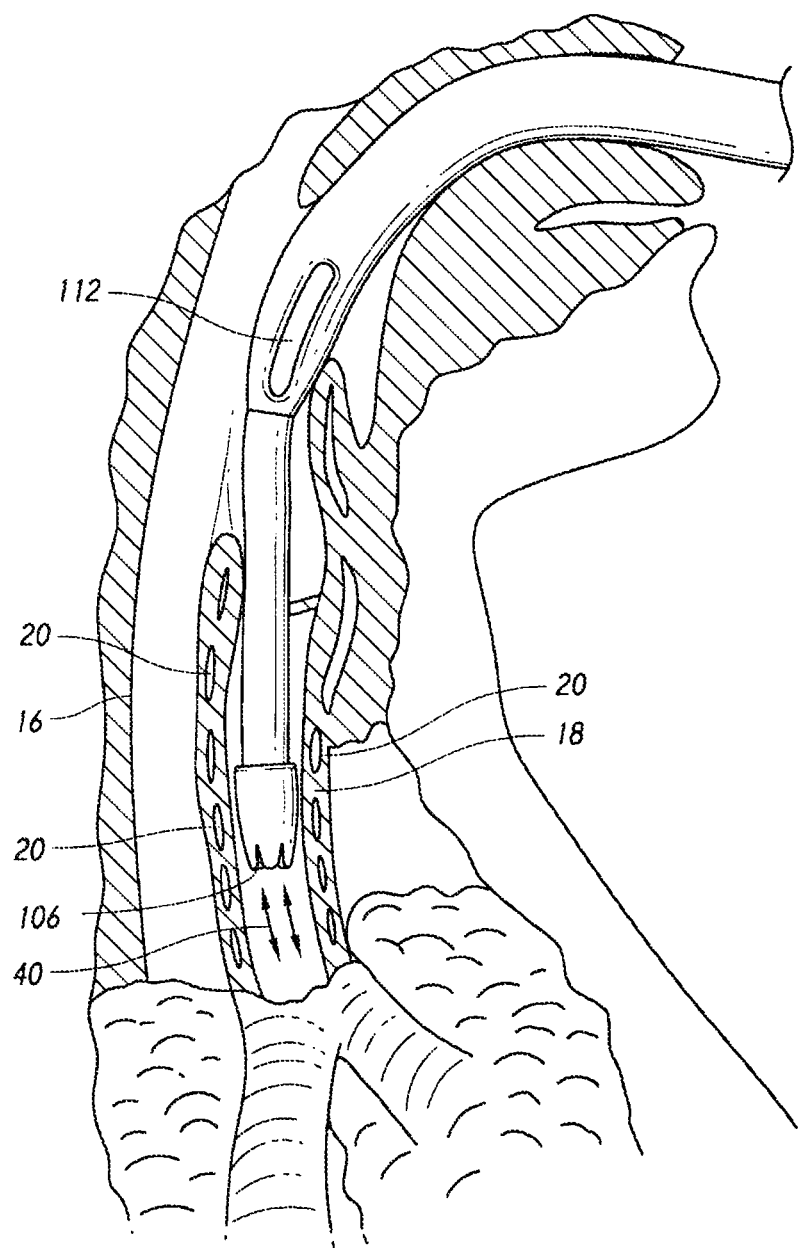

FIG. 5B illustrates the condition where the caregiver advances the working end 102 into a trachea 18 of an individual. Once the caregiver places the device 100, the caregiver can initiate the control unit 150 to start the process to determine placement of the device 100. Alternatively, one or more sensors on the device can automatically trigger actuation of the control unit. In either case, the control unit draws a vacuum through the distal opening 106 for a predetermined period of time. The vacuum reduces pressure and draws air within the distal opening 106. The control unit 150 then assess a state of the device by monitoring the vacuum, airflow, or any other fluid parameter that would indicate whether the walls of the body passage, in this case the trachea 18, collapsed causing the formation of a vacuum seal. In those cases like FIG. 5B where the device is situated within the trachea, the suction 30 will have little effect on the walls of the trachea 18. As noted above, the walls of the trachea 18 are reinforced with rings of cartilage 20 that provide structural rigidity of the airway. Because the controller 150 will not detect the formation of a vacuum seal at the distal opening 106 (or within the first lumen) the system registers the distal opening 106 as being properly positioned in the trachea 18 (rather than the esophagus 16) and, after a pre-determined period of time (e.g., 10-15 seconds), the controller 150 ceases to draw a vacuum and begins to ventilate the patient's lungs by alternating between delivery of the gas from the gas supply 160 and removing carbon dioxide. As a result, the first lumen is used as a ventilation lumen. It will be important for the controller 150 to differentiate changes in vacuum or flow that result from suctioning of fluids or debris. In some variations of the device, the controller 150 is configured to identify formation of a seal when the vacuum builds or flow drops to a sufficient degree such that the device has formed a vacuum seal rather than suctioned fluids or a substance.

The control unit 150 can determine whether or not a seal is formed by measuring strain on a suction motor (or similar apparatus such as a venturi device that produces a vacuum) that causes the negative pressure within the main lumen for suction. If the control unit 150 observes zero or minimal strain on the suction motor after a pre-determined time, then the control unit 150 will use the first lumen as the ventilation lumen.

Figure 5D:
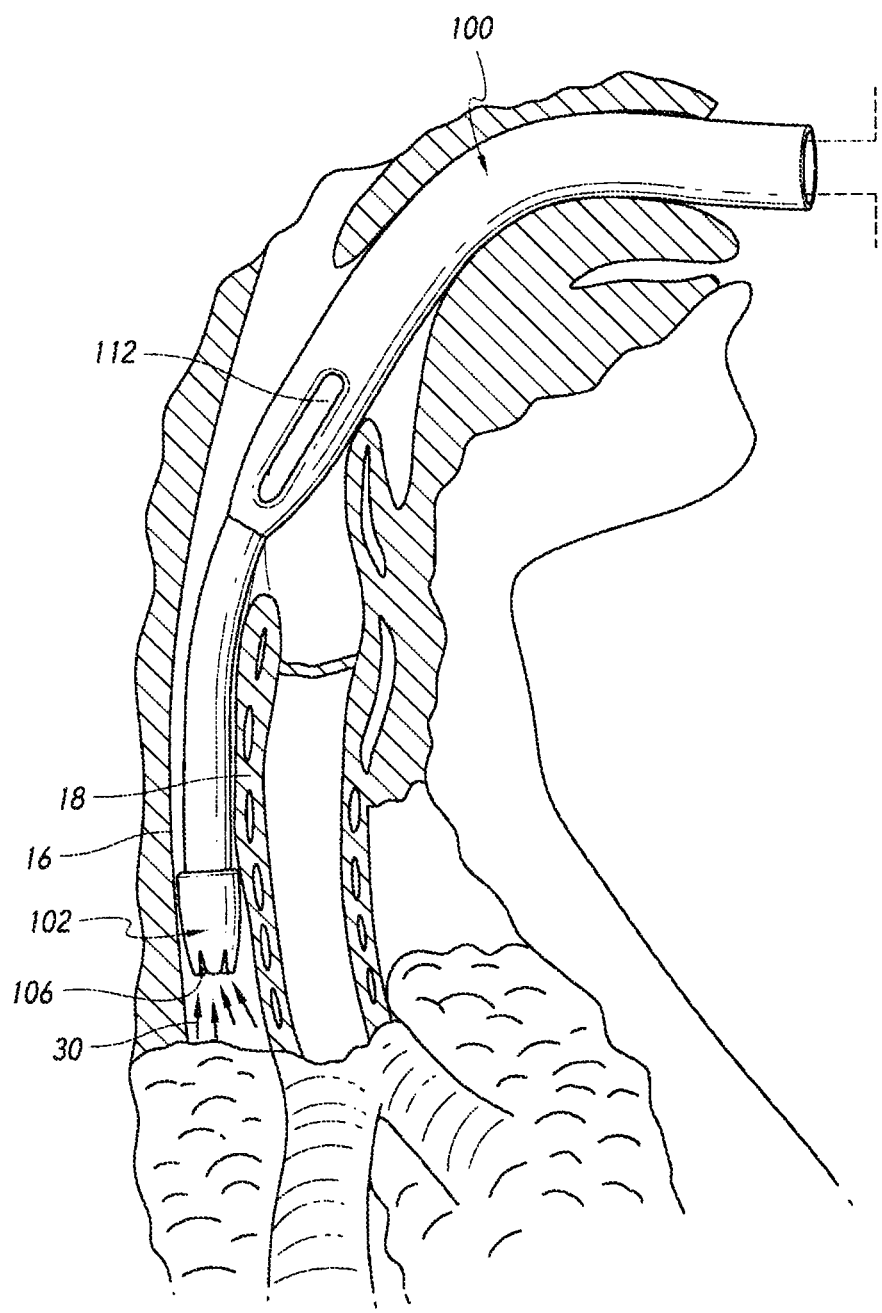

FIG. 5D illustrates a state where the caregiver advances a working end 102 of the ventilation device 100 into an esophagus 16 rather than the trachea 18. Similarly to the state depicted by FIG. 5B above, once the caregiver positions the device 100, the caregiver can initiate the control unit 150 to start the process to determine placement of the device 100. As noted above, additional variations of the device and system can include one or more sensors that can automatically trigger actuation of the control unit.

Figure 5E:
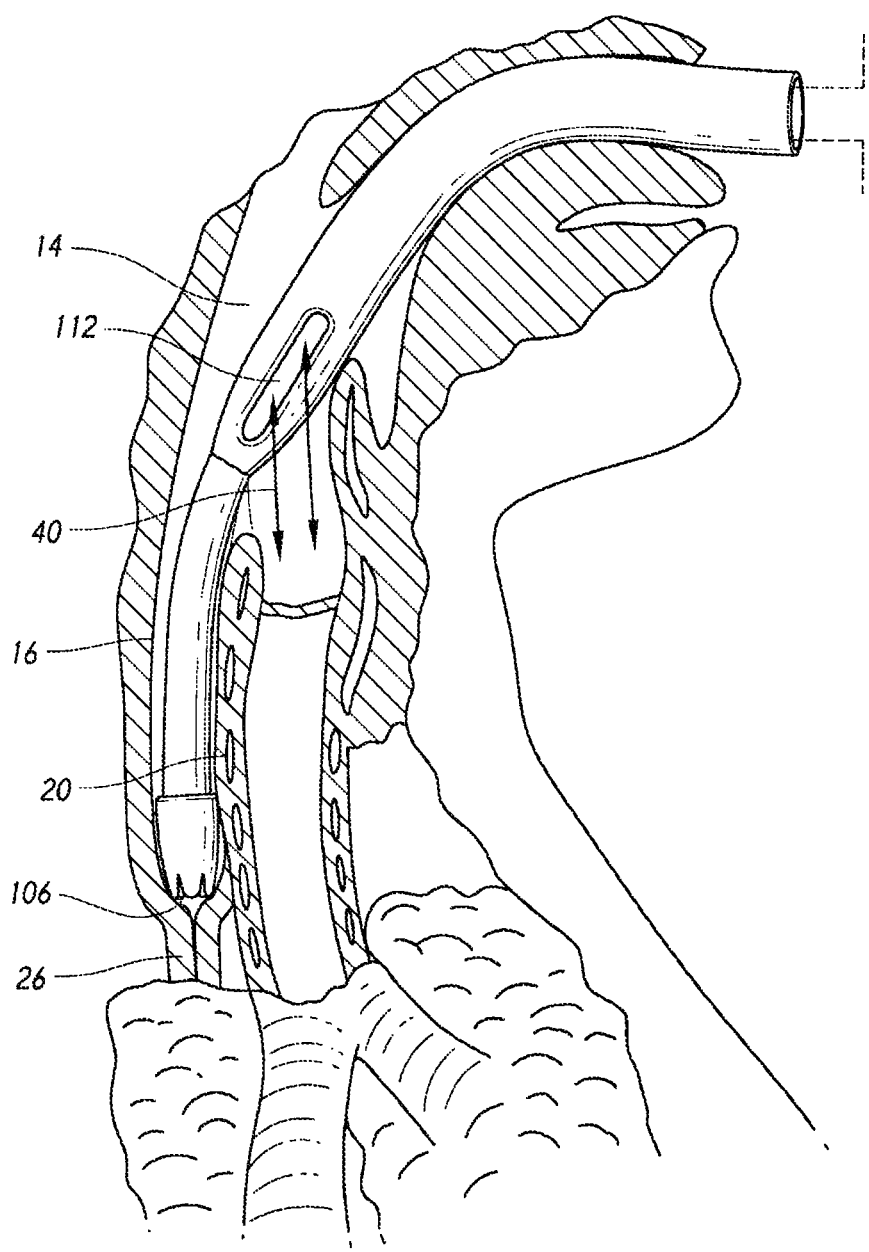

FIG. 5D depicts the state where the control unit 150 pull vacuum through the distal opening 106 for a predetermined period of time. The vacuum reduces pressure and draws air within the distal opening 106. The control unit 150 then assess a state of the device by monitoring the vacuum, airflow, or any other fluid parameter that would indicate whether the walls of the body passage, in this case the esophagus 16 collapsed. As shown, the walls partially or totally collapse resulting in formation of a vacuum seal at the distal opening 16. As noted above, muscles form the walls of the esophagus 16. There is no reinforcing structure in the esophagus as opposed to the cartilage rings in the trachea 18. The control unit can be configured to monitor the formation of a vacuum seal and if the seal remains for a predetermined period of time, the control unit 150 directs ventilation 40 in and out of the medial opening 112 as depicted in FIG. 5E. As shown and discussed above, the spacing between the distal opening 106 and medial opening 112 can be selected such that the medial opening remains in or near the pharynx 14. However, variations of the device permit the medial opening to enter the esophagus 16 so long as the opening 112 can continue to ventilate the patient. If the device is in the esophagus the device will seal the esophagus by creating vacuum through the distal end lumen, thus collapsing the esophagus and keeping the ventilated air from going into the stomach.

Because the control unit 150 will not detect the formation of a vacuum seal at the distal opening 106 (or within the first lumen) the system registers the distal opening 106 as being properly positioned in the trachea 18 (rather than the esophagus 16) and, after a pre-determined period of time, the control unit 150 ceases to draw a vacuum and begins to ventilate the patient's lungs by alternating between delivery of the gas from the gas supply 160 and removing carbon dioxide. In this situation the device uses the second lumen as a ventilation lumen. One additional benefit of positioning the working end 102 of the device 100 within the esophagus 16 is that the vacuum seal produces an anchoring effect that maintains the device in position. This feature eliminates the need to secure the mask or other feature about the patient's head, neck or face. In addition, if a caregiver inadvertently pulls the device 100 while a seal is formed, the vacuum seal is simply broken and the device releases from the esophagus 16. This provides a safety improvement over conventional ventilation devices that rely on an expandable balloon, which if pulled, can cause trauma to the patient's airways, vocal cords, or other structures.

In certain variations, the device 100 shall cease ventilating after a period of time and produce suction through the distal opening. Such a step is considered a safety feature in the event that the working end is moved, repositioned, etc.

Figure 6A:
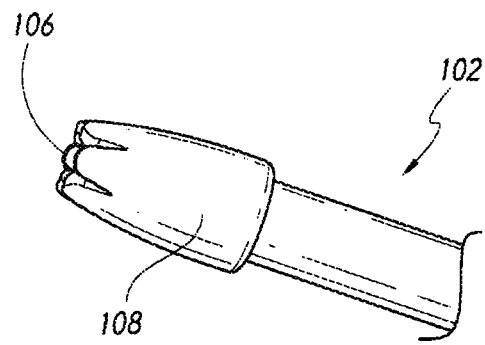
FIGS. 6A to 6C show additional variations of a working end of a ventilation device.
Figure 6B:
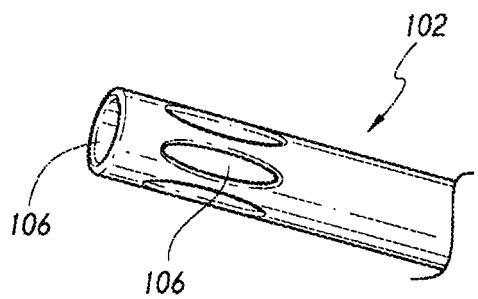
Figure 6C:
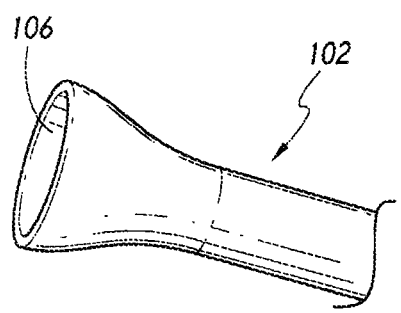

FIGS. 6A to 6C show variations of the working end 102 of a ventilation device as described herein. FIG. 6A illustrates a hub having an opening 106 that is surrounded by a contoured surface. The contoured surface can assist reducing the chance that the distal opening 106 becomes clogged due to food particles or other fluids. This feature also assists in reducing the occurrences that the control unit misreads an opening 106 that is obstructed (with food particles or other bodily fluids) for an opening that formed a seal with the walls of the esophagus. FIGS. 6B and 6C illustrate additional variations of a working end 102 of a ventilation device. In these variations, the working end 102 can be fabricated with or without a hub. FIG. 6B illustrates a straight tube having a plurality of openings 106. FIG. 6C illustrates a beveled end having an opening 106.

Figure 7:
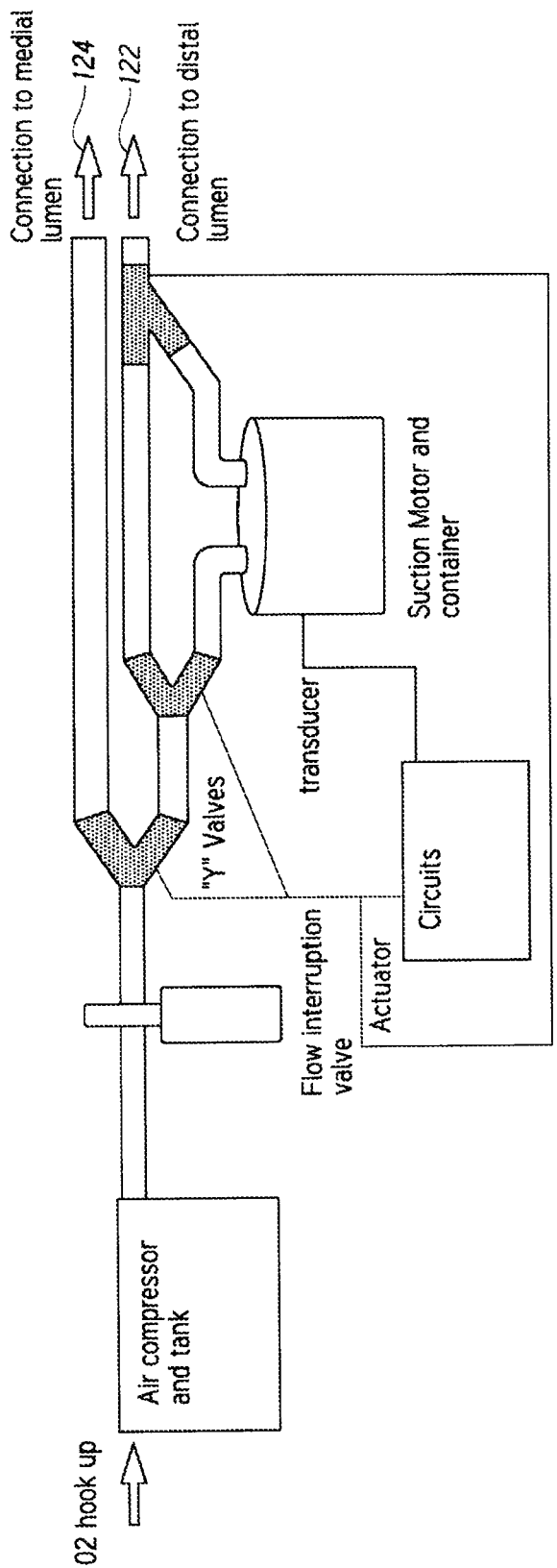
FIG. 7 illustrates a schematic of an electrically powered system.

As noted above, the device described herein can be pneumatically driven using compressed gas and valves or electrically controlled. FIG. 7 illustrates a schematic of an electrically powered device using a suction motor, air compressor and circuitry to switch between a first fluid path 122 (ultimately fluidly coupled to a distal opening) and a second fluid path 124 (ultimately fluidly coupled to a medial opening).

Figure 8A:
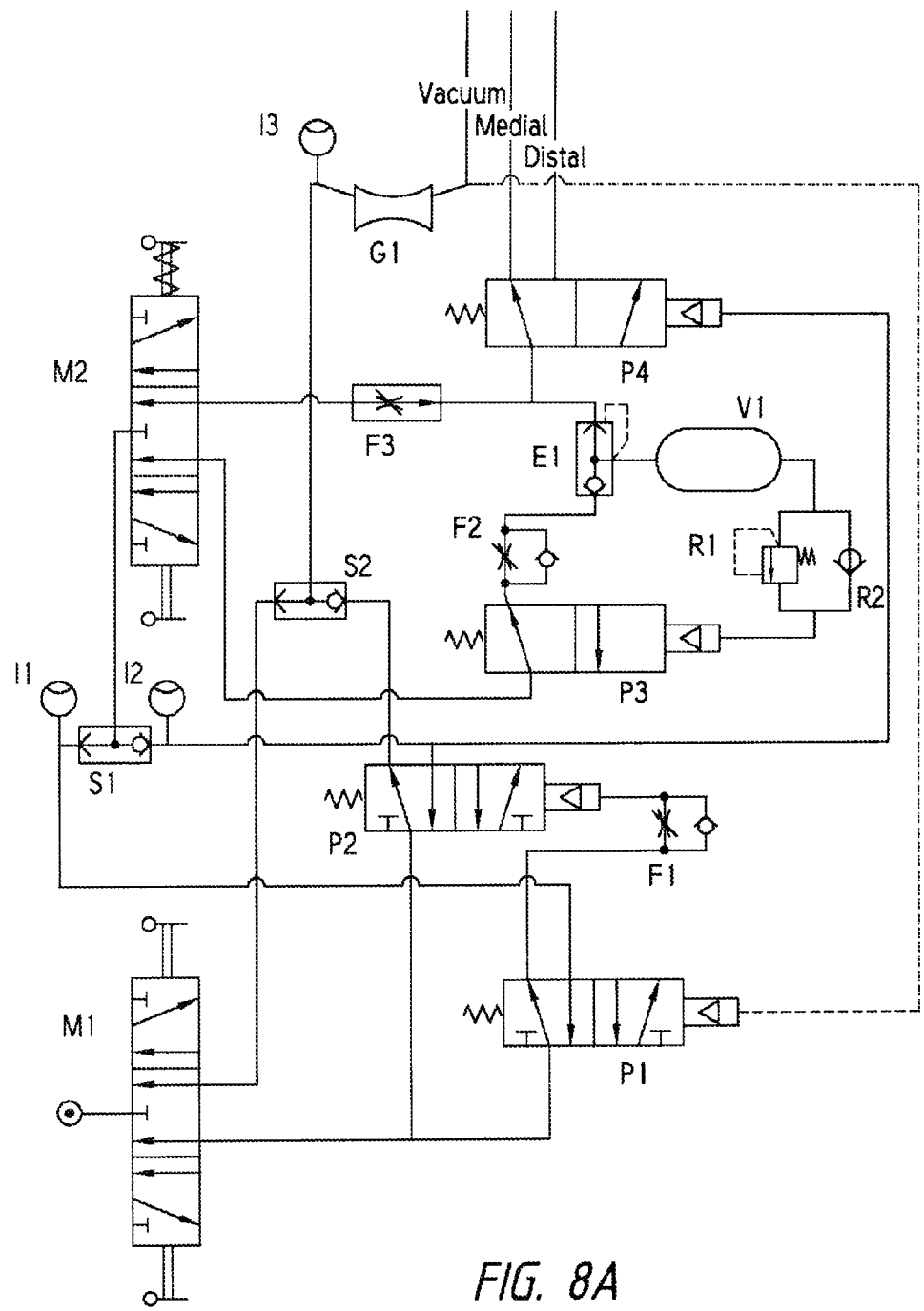
FIG. 8A shows an example of a component schematic for a pneumatically driven system as described herein.

FIG. 8A shows an example of a component schematic for a system as described herein that is pneumatically driven. FIG. 8B provides a list of the components found in FIG. 8A. The valves operate in multiple states based on the conditions discussed above. The following description illustrates an example of the different states of the components found in the component schematic of FIG. 8A.

Medial Supply Valve P1 (4/2);
  State 1 (nominal, spring return): Controls the 15 s timing of vacuum supply through Distal Supply Valve P2;
  State 2 (actuated): Provides supply for medial ventilation;
  Pilot Actuation: 10" Hg vacuum
Distal Supply Valve P2 (4/2)
  State 1 (nominal, spring return): Provides supply for Vacuum Generator;
  State 2 (actuated): Provides Supply for Distal Ventilation;
  Pilot Actuation: 40 psi from flow-controlled output of Medial Supply Valve, State 1.
Pulse Valve P3 (3/2 Normally Open);
  State 1 (nominal, spring return): Fills Accumulator volume at flow-controlled rate until set pressure is achieved at inline Relief Valve;
  State 2: (actuated): Dumps accumulator volume to Ventilation Selector Valve through quick exhaust;
  Pilot Actuation: 5 psi from output of inline Relief Valve
Ventilation Selector Valve P4 (3/2 Fully Ported);
  State 1 (nominal, spring return): Routes output of Pulse Valve to Medial Ventilation Output;
  State 2: (actuated): Routes output of Pulse Valve to Distal Ventilation Output;
  Pilot Actuation: 40 psi from output of Distal Supply Valve, State 2

Operation Valve M1 (Manual Toggle, 3 position, All Detent);
  State 1 (toggle down, "ON"): Provides supply for Medial Supply Valve and Distal Supply Valve;
  State 2 (toggle centered, "OFF/RESET"): Blocks supply, vents system;
  State 3 (toggle up, "VACUUM"): Bypasses all valves, provides supply to Vacuum Generator.
Mode Valve M2 (Manual Toggle, 3 position, Detent/Detent/Momentary);
  State 1 (toggle down, detent, "VENTILATE"): Provides supply for Pulse Valve and Ventilation Selector Valve;
  State 2 (toggle centered, detent, "BYPASS"): Blocks supply to Pulse Valve and Ventilation Selector Valve.
  State 3 (toggle up, momentary spring return, "ON-DEMAND"): Blocks supply to Pulse Valve, provides continuous flow-controlled supply to Ventilation Selector Valve The system illustrated by the component schematic of FIG. 8A can have a variety of modes of operation. In one example, as shown by FIG. 8C, the system can include 8 separate modes of operations controlled by the position of various valves and the operation state of a medial supply valve.

Figure 8E:
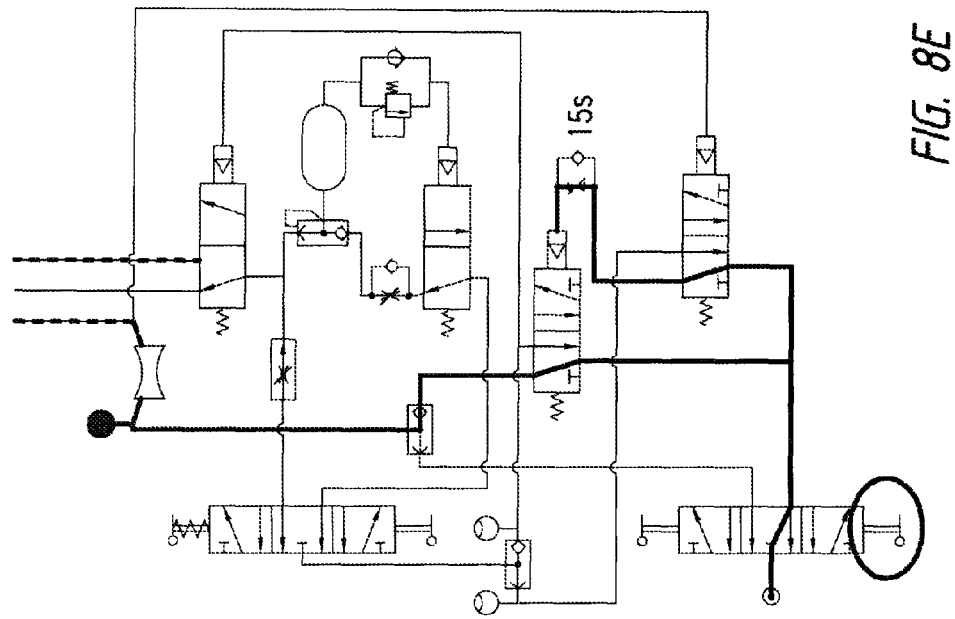
FIGS. 8D to 8M illustrates various flow paths for the various modes of operation.
Figure 8D:
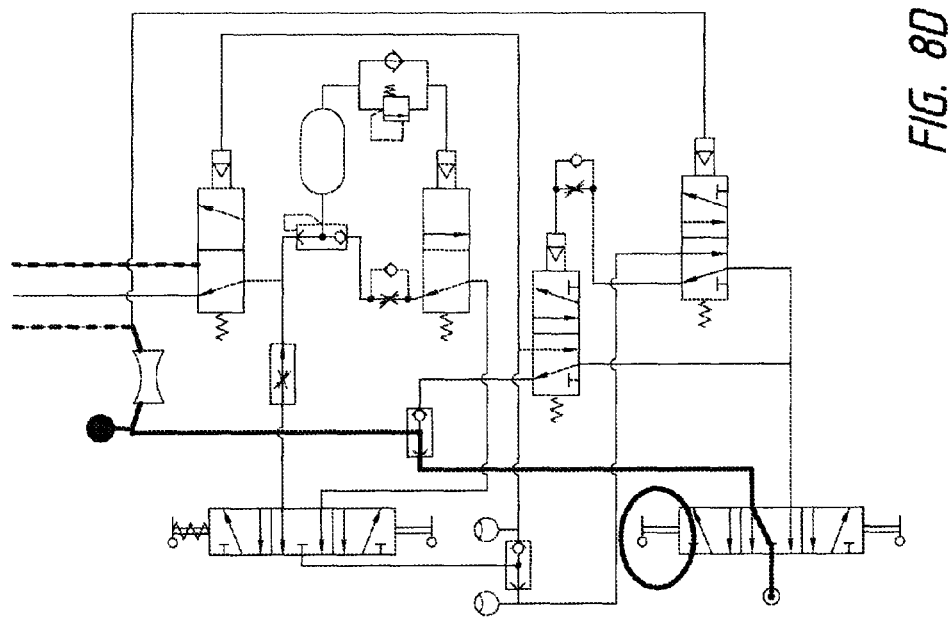

Mode 0, where the system is set to an Off position.
  M1 set to OFF;
  Main supply blocked; system vented;

FIG. 8D shows Mode 1, where there is a continuous vacuum applied through the system.
  M1 set to VACUUM
  Ventilation system bypassed; vacuum at Vacuum Output; Vacuum Indicator on FIG. 8E shows Mode 2, where the system engages in placement detection;
  M1 set to ON;
  Vacuum at Vacuum Output until P2 pilot activated (15 s); Vacuum Indicator on;

In Mode 3, the system engages in ventilation through the distal opening.
  M1 set to ON; M2 set to VENTILATE;
  No vacuum detected; P2 pilot activated; P4 pilot activated.

Figure 8G:
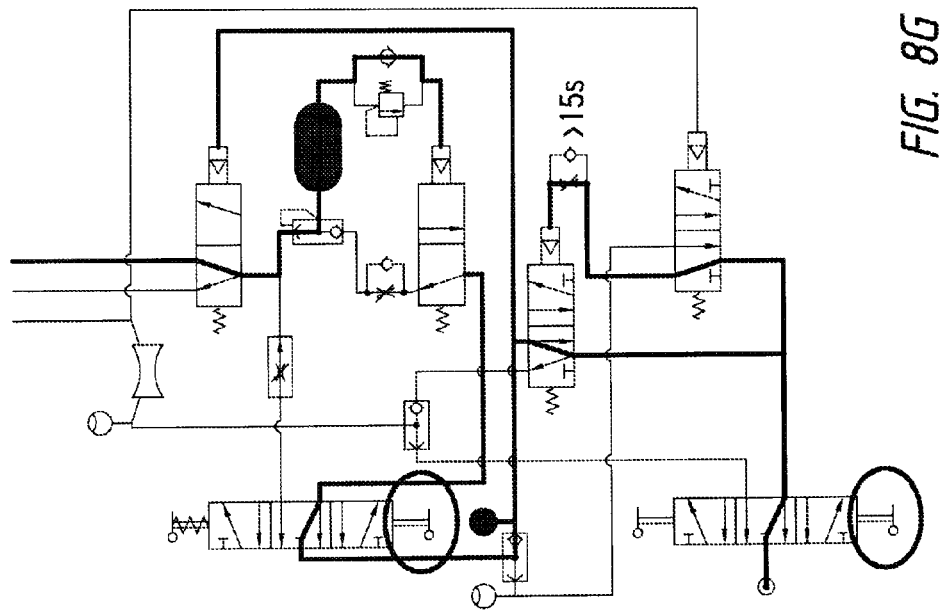
Figure 8F:
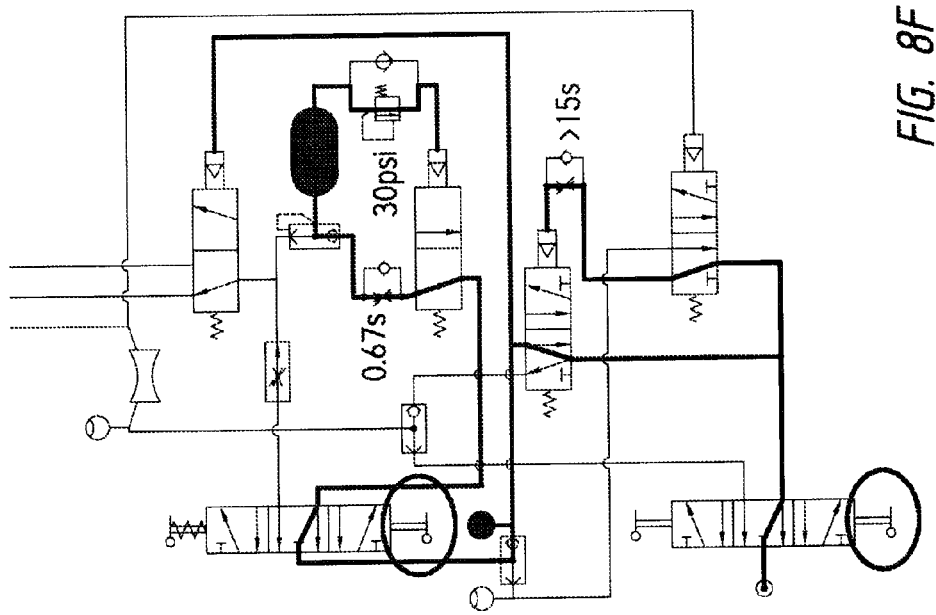

FIG. 8F shows Mode 3A, where an accumulator fills at controlled rate (0.67 s) until inline Relief Valve activates (30 psi);
  Distal Ventilation Indicator on.

FIG. 8G shows Mode 3B: P3 pilot activates, closing P3 and exhausting Accumulator volume through Quick Exhaust to P4; Distal Ventilation Indicator on.

Mode 4—Medial Ventilation
  M1 set to ON; M2 set to VENTILATE
  Vacuum detected; P1 pilot activated; vacuum at Vacuum Output.

Figure 8I:
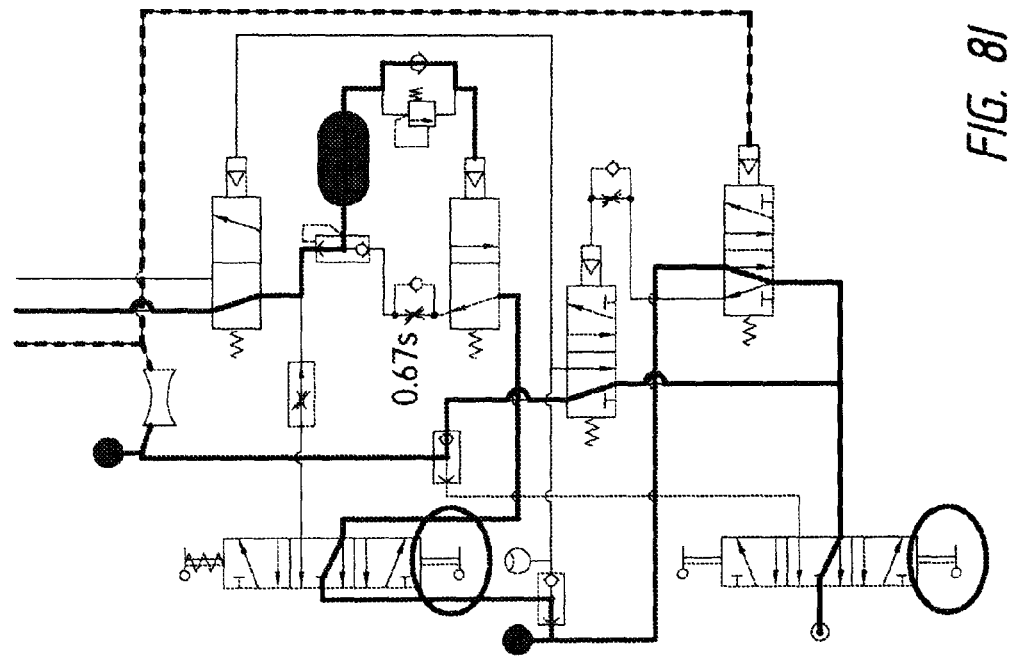
Figure 8H:
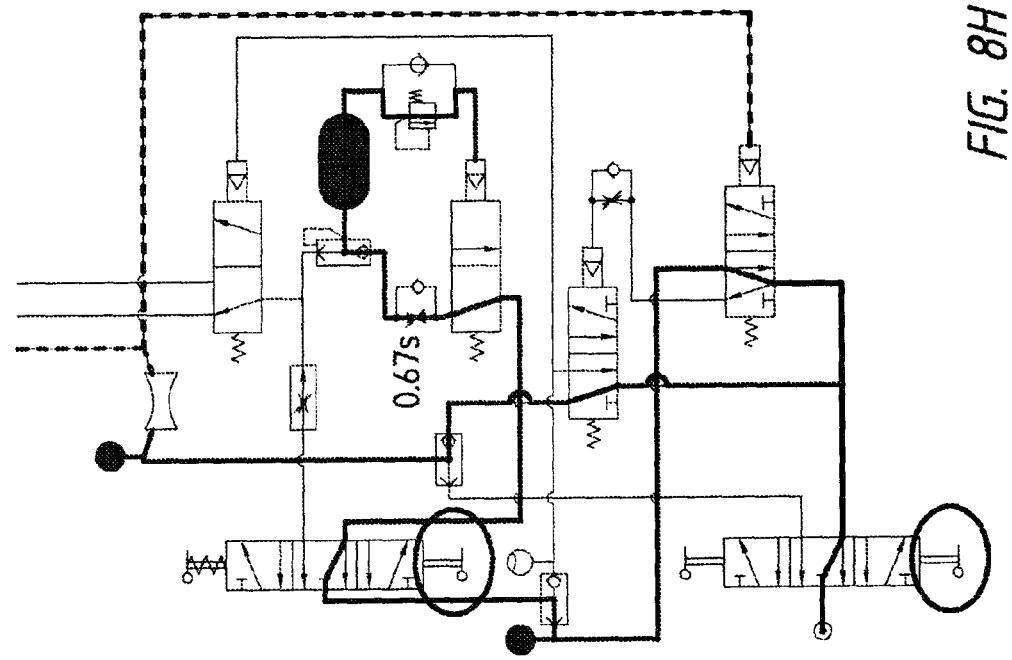

FIG. 8H shows Mode 4A where accumulator fills at controlled rate (0.67 s) until inline Relief Valve activates (30 psi);
  Vacuum Indicator on;
  Medial Ventilation Indicator on.

FIG. 8I shows Mode 4B: P3 pilot activates, closing P3 and exhausting Accumulator volume through Quick Exhaust to P4;
  Vacuum Indicator on; Medial Ventilation Indicator on.

Figure 8K:
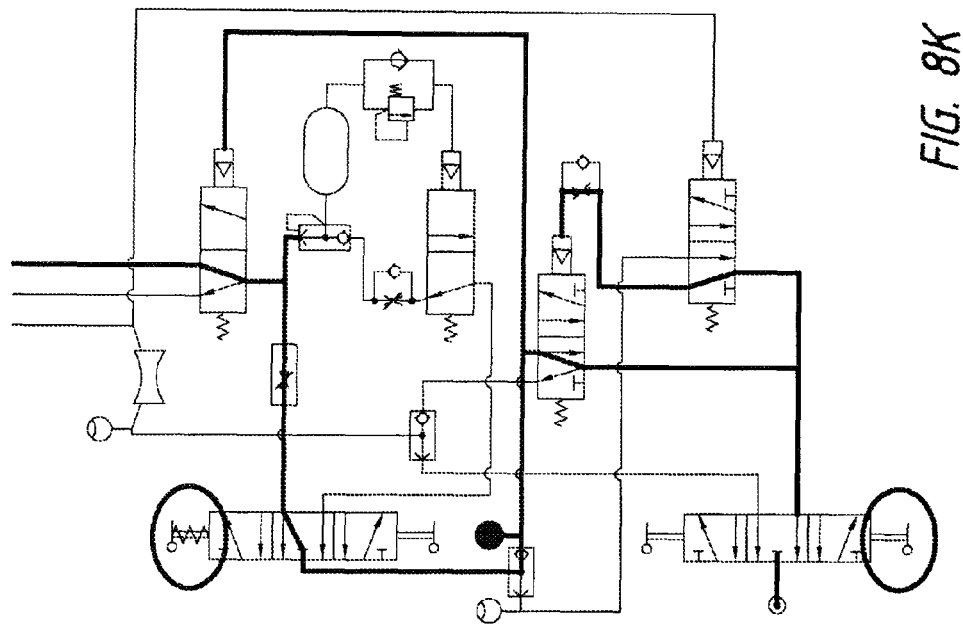
Figure 8J:
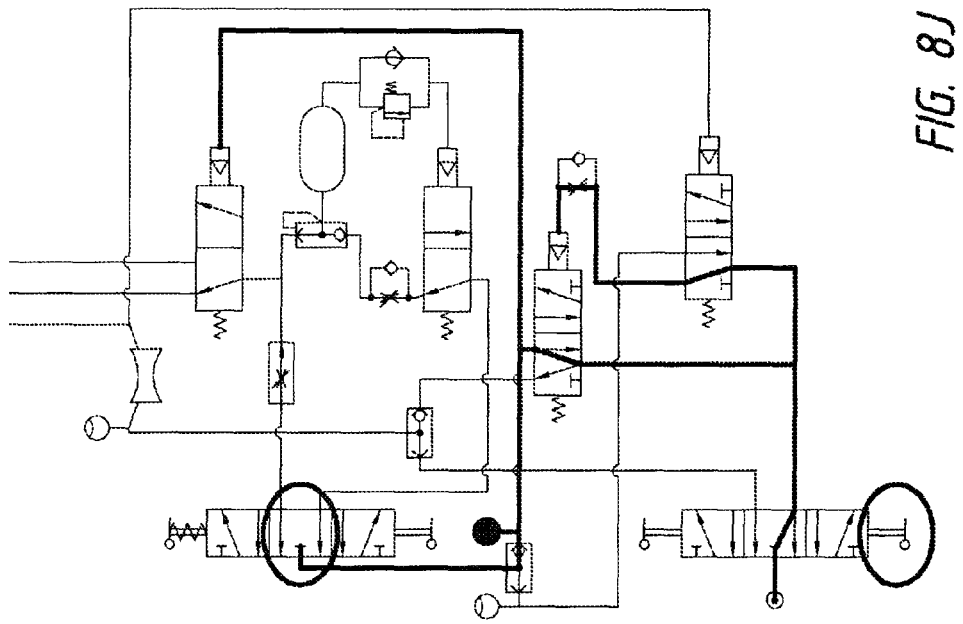

FIG. 8J shows Mode 5—Ventilation Bypass (Distal);
  M1 set to ON; M2 set to BYPASS;
  No vacuum detected; P2 pilot activated; P4 pilot activated; supply to P3 & P4 blocked; Distal Ventilation Indicator on.

Figure 8M:
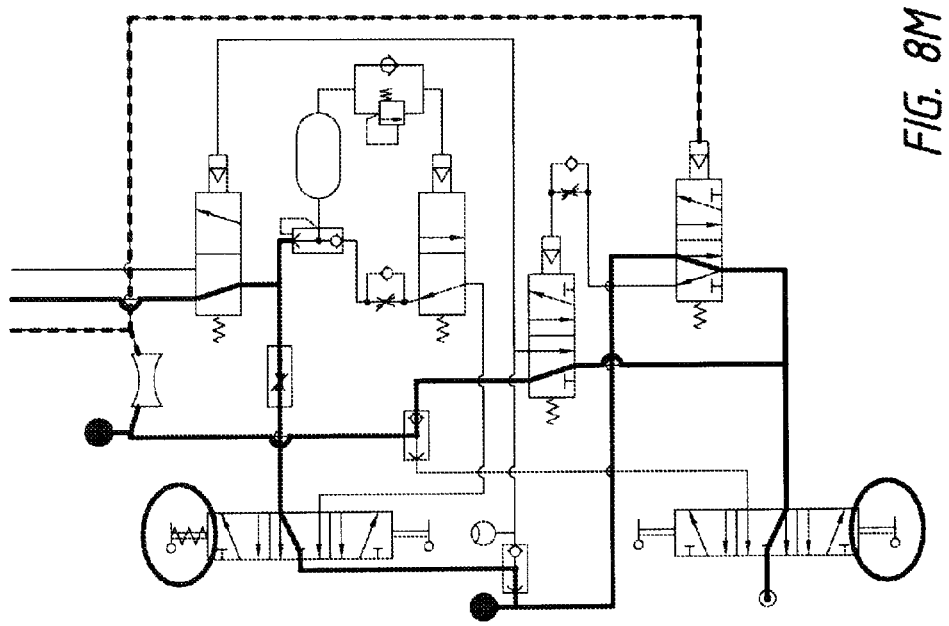
Figure 8L:
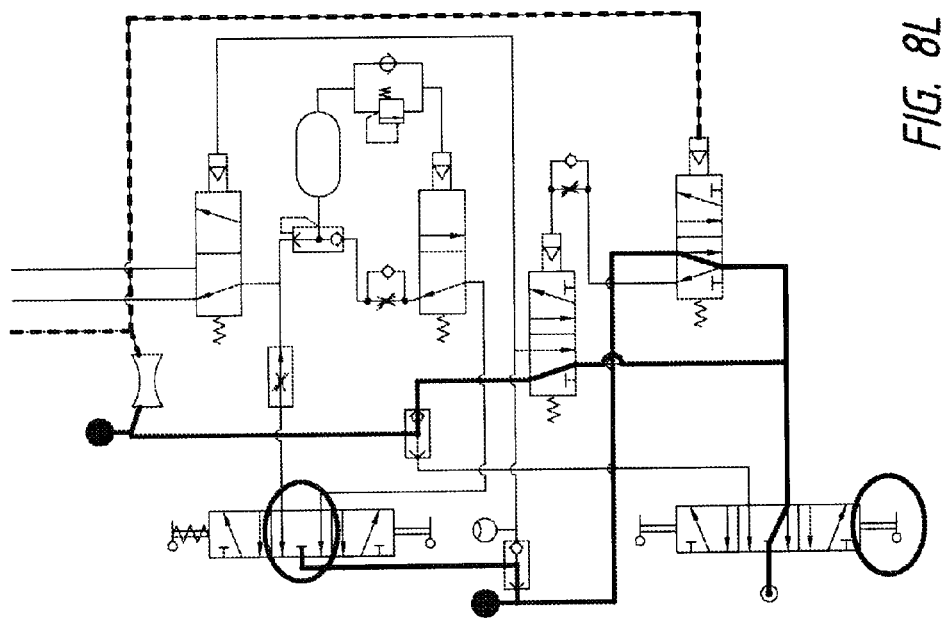

FIG. 8K shows Mode 6—On-Demand Ventilation (Distal);
  M1 set to ON; M2 set to ON-DEMAND;
  No vacuum detected; P2 pilot activated; P4 pilot activated; supply to P3 blocked; continuous flow-regulated flow to P4; Distal Ventilation Indicator on FIG. 8L shows Mode 7—Ventilation Bypass (Medial);
  M1 set to ON; M2 set to BYPASS;
  Vacuum detected; P1 pilot activated; vacuum at Vacuum Output;
  supply to P3 blocked;
  Vacuum Indicator on;
  Medial Ventilation Indicator on FIG. 8M shows Mode 8—On-Demand Ventilation (Medial);
  M1 set to ON; M2 set to ON-DEMAND;
  Vacuum detected; P1 pilot activated; vacuum at Vacuum Output;
  supply to P3 blocked;
  continuous flow-regulated flow to P4; Vacuum Indicator on; Medial Ventilation Indicator on.

The preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. The scope of the present invention, therefore, is not intended to be limited to the exemplary embodiments shown and described herein. Rather, the scope and spirit of present invention is embodied by the appended claims.

It must be noted that as used herein and in the appended claims, the singular forms "a", "an", and "the" include plural referents unless the context clearly dictates otherwise. Thus, for example, reference to "a string" may include a plurality of such strings and reference to "the tubular member" includes reference to one or more tubular members and equivalents thereof known to those skilled in the art, and so forth.

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

All publications mentioned herein are incorporated herein by reference to disclose and describe the methods and/or materials in connection with which the publications are cited. The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

That which is claimed is:

1. A method for ventilating an individual, the method comprising:
    inserting a ventilation device within a natural respiratory opening of the individual by advancing a working end of the ventilation device within a body passageway of the individual, where the working end includes a distal opening fluidly coupled to a first lumen and a medial opening fluidly coupled to a second lumen;
    drawing suction through the distal opening to induce collapse of the body passageway and maintaining the suction for a period of time;
    monitoring a fluid parameter to determine whether the body passageway collapses;
    ventilating the individual through the second lumen upon detecting collapse of the body passageway while maintaining suction to maintain the collapse of the body passageway to prevent fluid from passing through the collapsed body passageway; and
    ventilating the individual through the first lumen upon failure to detect collapse of the body passageway.

2. The method of claim 1, further comprising adjusting a ventilation parameter to improve ventilation of the individual where the ventilation parameter comprises a parameter selected from the group consisting of a ventilation rate, volume, pressure, inhale and exhale ratios, and PEEP.

3. The method of claim 1, further comprising timing ventilating the individual with a chest compression to increase effectiveness of both the compression and ventilation.

4. The method of claim 1, further comprising initially ventilating through the second lumen during application of suction through the first lumen.

5. The method of claim 1, further comprising, upon detecting collapse of the body passage, maintaining sufficient suction to temporarily anchor the ventilation device within the body passageway.

6. The method of claim 1, further comprising a balloon coupled to the working end of the ventilation device, where the balloon temporarily anchors the ventilation device within the body passageway.

7. The method of claim 1, where a proximal portion of the ventilation device further comprises a face mask, where the distance between the face mask and the distal opening is adjustable.

8. The method of claim 1, where a proximal portion of the ventilation device further comprises a reinforced section to prevent collapse of the ventilation device in a mouth of the individual.

9. The method of claim 1, where a proximal portion of the ventilation device further comprises a pressure relief valve to adjust ventilation parameters of the individual.

10. The method of claim 1, where the ventilation device comprises a plurality of markings on an exterior surface and where inserting the ventilation device into the natural respiratory opening comprises advancing the ventilation device to a depth determined by one or more markings.

11. The method of claim 1, further comprising coupling a collection member to the first lumen and collecting bodily fluids in the collection member during suctioning.

12. A method for rapidly ventilating an individual experiencing respiratory distress, the method comprising:
    inserting a ventilation device within a natural respiratory opening of the individual by advancing a working end of the ventilation device within a body passageway of the individual, where the working end includes a distal opening fluidly coupled to a first lumen and a medial opening fluidly coupled to a second lumen;
    pulling a suction force to induce collapse of the body passageway through the distal opening and maintaining the suction force for a period of time;
    monitoring a fluid parameter to determine whether the body passageway collapses;
    ventilating the individual through the first lumen in the event that collapse of the body passageway is not detected and, ventilating the individual through the second lumen upon detecting collapse of the body passageway while maintaining suction to maintain the collapse of the body passageway to prevent fluid from passing through the collapsed body passageway.

13. The method of claim 12, further comprising initially ventilating through the second lumen during application of suction through the first lumen.

14. The method of claim 12, further comprising deploying an anchor to temporarily secure the ventilation device in the body passageway.

15. The method of claim 14, where the anchor comprises a balloon coupled to the working end of the ventilation device.

16. The method of claim 12, where a proximal portion of the ventilation device further comprises a reinforced section to prevent collapse of the ventilation device in a mouth of the individual.

17. The method of claim 12, where a proximal portion of the ventilation device further comprises a pressure relief valve to adjust ventilation parameters of the individual.

18. The method of claim 12, where the ventilation device comprises a plurality of markings on an exterior surface and where inserting the ventilation device into the natural respiratory opening comprises advancing the ventilation device to a depth determined by one or more markings.

19. The method of claim 12, further comprising coupling a collection member to the first lumen and collecting bodily fluids in the collection member during suctioning.

20. A device for ventilating an individual through one or more body passageways, the device comprising:
    a tubular member having at least a first and second lumen, where the first lumen is fluidly coupled to a first opening located towards a distal portion of the tubular member, the second lumen fluidly coupled to a medial opening being located proximally to the first opening along a wall of the tubular member, where the first opening and medial opening are fluidly isolated within the tubular member;
    a control system having a suction source and a gas supply lumen, the control system having a valve configured to fluidly couple the ventilation source to either the first lumen or to the second lumen; the control system also capable of drawing suction through the first opening and first lumen, where the control system is configured to monitor a fluid parameter of the ventilation source to determine collapse of the body passageway and formation of a seal at the first opening;
    where the control system is further configured to selectively form a ventilation path from the supply lumen to the first lumen or second lumen by
        selecting the first lumen as the ventilation path if collapse of the body passageway is not detected; and
        selecting the second lumen as the ventilation path if collapse of the body passageway is detected; and
    where the control system is capable of ventilating the individual through the ventilation path and maintains suction while ventilating through the second lumen to prevent fluid from passing through the collapsed body passageway.

21. The device of claim 20, further comprising providing an indicator signal to identify desired times of chest compression.

22. The device of claim 20, further comprising an anchor to temporarily secure the tubular member in a body passageway.

23. The method of claim 22, where the anchor comprises a balloon coupled to the working end of the ventilation device.

24. The device of claim 20, where the tubular member further comprises a reinforced section to prevent collapse of the ventilation device in a mouth of the individual.

25. The device of claim 20, where the control system further comprises a pressure relief valve to adjust ventilation parameters of the individual.

26. The device of claim 20, where the tubular member comprises a plurality of markings on an exterior surface and where the ventilation device is configured to be advanced to a depth determined by one or more markings.

* * * * *